(12) United States Patent
Bhargava

(10) Patent No.: US 10,143,416 B2
(45) Date of Patent: Dec. 4, 2018

(54) QUANTITATION AND DISPLAY OF IMPEDANCE DATA FOR ESTIMATING GASTROENTEROLOGY TRACT PARAMETERS

(71) Applicant: The Regents of the University of California, Oakland, CA (US)

(72) Inventor: Valmik Bhargava, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 14/450,208

(22) Filed: Aug. 1, 2014

(65) Prior Publication Data

US 2015/0038805 A1    Feb. 5, 2015

Related U.S. Application Data

(60) Provisional application No. 61/861,319, filed on Aug. 1, 2013.

(51) Int. Cl.
*A61B 8/00* (2006.01)
*A61B 5/103* (2006.01)
(Continued)

(52) U.S. Cl.
CPC ............ *A61B 5/4205* (2013.01); *A61B 5/037* (2013.01); *A61B 5/0538* (2013.01);
(Continued)

(58) Field of Classification Search
CPC . A61B 5/02007; A61B 5/0535; A61B 5/4233; A61B 5/1076; A61B 5/204; A61B 5/0538
(Continued)

(56) References Cited

U.S. PATENT DOCUMENTS 6,360,123 B1    3/2002 Kimchi et al.
2004/0254495 A1    12/2004 Mabary et al.
(Continued)

FOREIGN PATENT DOCUMENTS

WO    WO-2012034168 A1    3/2012

OTHER PUBLICATIONS

International Search Report and Written Opinion for International Application No. PCT/US14/49495, dated Dec. 5, 2014. (11 pages).

*Primary Examiner* — Jeffrey G Hoekstra
*Assistant Examiner* — Jonathan M Foreman
(74) *Attorney, Agent, or Firm* — Mintz Levin Cohn Ferris Glovsky and Popeo, P.C.

(57) ABSTRACT

A method for characterization of a patient's esophagus may include receiving data measured by an impedance and high resolution manometry catheter in an esophagus in which the data may be representative of a pressure and/or an impedance associated with a swallowing event. The method may also include determining a cross-sectional area of the esophagus based on the received data and a pre-determined amount of a bolus consumed during the swallowing event. Systems and apparatus for characterizing a patient's esophagus may also include measuring data with a high resolution manometry catheter to determine the cross-sectional area, work, and compliance of the esophagus as a function of time during a swallowing event. Averaged data may establish a database of normal values for work done and compliance and allow for comparison of a patient to normal pathology.

20 Claims, 11 Drawing Sheets
(10 of 11 Drawing Sheet(s) Filed in Color)

(51) Int. Cl.
*A61B 5/117* (2016.01)
*A61B 5/00* (2006.01)
*A61B 5/053* (2006.01)
*A61B 5/107* (2006.01)
*A61B 5/03* (2006.01)
*A61B 8/12* (2006.01)

(52) U.S. Cl.
CPC .......... *A61B 5/1076* (2013.01); *A61B 5/4233* (2013.01); *A61B 5/7278* (2013.01); *A61B 5/743* (2013.01); *A61B 8/12* (2013.01)

(58) Field of Classification Search
USPC .................................................. 600/547, 593
See application file for complete search history.

(56) References Cited

U.S. PATENT DOCUMENTS

| | | |
|---|---|---|
| 2005/0080832 A1 | 4/2005 | Stuebe et al. |
| 2009/0003669 A1 | 1/2009 | Parks et al. |
| 2009/0062684 A1* | 3/2009 | Gregersen et al. ........... 600/547 |
| 2010/0010355 A1 | 1/2010 | Kassab |
| 2011/0196255 A1* | 8/2011 | Kassab ........................ 600/549 |
| 2012/0053441 A1 | 3/2012 | Kassab |

* cited by examiner

QUANTITATION AND DISPLAY OF IMPEDANCE DATA FOR ESTIMATING GASTROENTEROLOGY TRACT PARAMETERS

CROSS-REFERENCE TO RELATED APPLICATION

This application claims priority to U.S. Provisional Patent Application No. 61/861,319, titled "QUANTITATION AND DISPLAY OF IMPEDANCE DATA FOR ESTIMATING GASTROENTEROLOGY TRACT PARAMETERS," filed Aug. 1, 2013, the disclosure of which is hereby incorporated by reference in its entirety.

BACKGROUND

There are numerous diseases associated with movement of material through the gastrointestinal tract, in particular the esophagus. To observe the movement of material, such as food or liquid, through the esophagus, the pressure exerted by the esophagus may be measured as the material moves through the center of the esophagus. This results in pressure values as a function of time and location of in the esophagus. In some cases, impedance measurements are also made along the esophagus. The measurements of the esophagus may allow physicians and caregivers to compare healthy, normal movement in the esophagus to abnormal or possibly diseased movement, as well as to monitor changes in an abnormal or diseased esophagus in response to medical treatment.

SUMMARY

Methods, systems, and apparatus, including computer program products, are provided for quantitation and display of impedance data, as well as processed data, for estimating gastroenterology tract parameters. In some example embodiments, there is provided a method that includes receiving data measured by an impedance and high resolution manometry catheter in an esophagus, the data representative of a pressure and/or an impedance associated with a swallowing event; and determining, based on the received data and a pre-determined amount of a bolus consumed during the swallowing event, a cross-sectional area of the esophagus.

In some variations, one or more of the features disclosed herein including the following features can optionally be included in any feasible combination. An indication of the predetermined amount of the bolus may be received, and an esophageal impedance may be determined. The determining may include generating a plot of a pressure versus a cross-sectional area loop for at least one distinct segment of the esophagus at discrete time points during the swallowing event and determining an area for each pressure versus cross-sectional area loop plotted. A display of the determined cross-sectional area may be generated, wherein the display includes at least a plot of pressure exerted by the esophagus as a function of location along the esophagus and as a function of time. An average value for work done by a segment of the esophagus may be determined based on the cross-sectional area and pressure exerted by the segment from two or more swallowing events, wherein the bolus consumed was substantially a same volume for each swallowing event. A calculation of the percent of the total work of the esophagus done by each segment of the esophagus may made and averaged over two or more swallowing events. An average work may be determined for two or more patients identified as normal to generate a reference work profile. A work done by the esophagus of a patient with a disease may be compared with the reference work profile. An average value for segmental compliance of the esophagus may be determined based on the cross-sectional area, or esophageal segmental volume, and pressure exerted by the segment from two or more swallowing events, wherein the bolus consumed was substantially a same volume for each swallowing event. At least one of the cross-sectional area, a cross-sectional diameter, or a pressure may be rendered as a time-lapse movie. A plurality of cross-sectional area calculations for a plurality of segments of the esophagus are based on the same predetermined bolus value. The cross-sectional area, or a derived diameter, may be rendered as the width of the esophagus in a time-lapse movie. Polynomial curve fitting, cubic spline, and other techniques may be used to smooth the edges of a time-lapse movie that renders the cross-sectional area, or a cross-sectional diameter, and pressure of an esophagus. A three-dimensional rendering of an esophagus during one or more swallowing events may rotate to be viewed in any orientation. Smoothing techniques including mesh smoothing may be used in creating a three-dimensional rendering of an esophagus.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The aspects described above and other aspects will now be described in detail with reference to the following drawings.

Like reference symbols in the various drawings indicate like elements.

DETAILED DESCRIPTION

Figure 1:
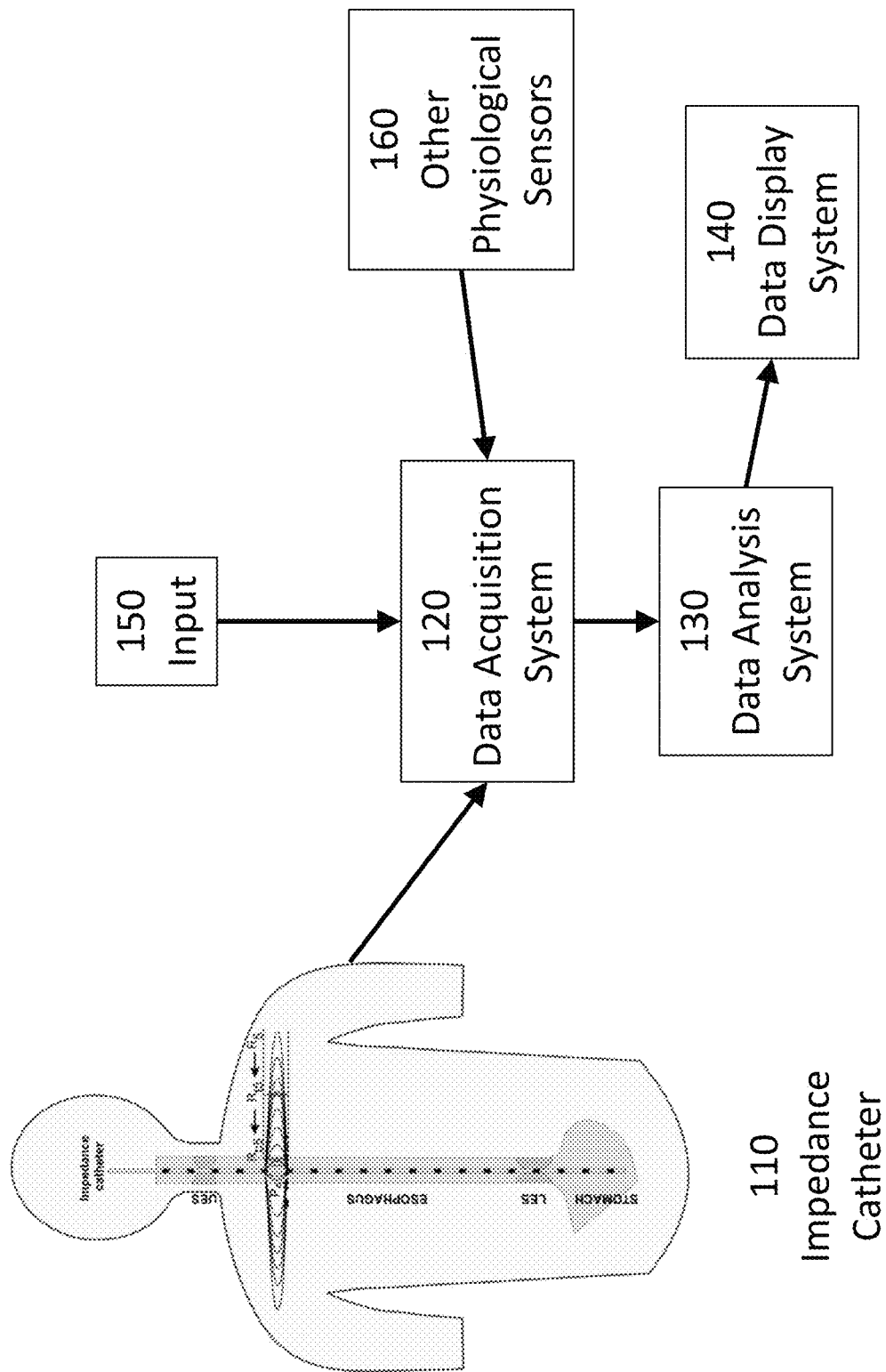
FIG. 1 depicts an example system for quantitation of a cross-sectional area of an esophagus.

The subject matter disclosed herein may provide, in some example embodiments, a process for quantitating the cross-sectional area (CSA) or the segmental volume of the esophagus.

Moreover, the subject matter disclosed herein may, in some example embodiments, derive one or more parameters, which can be displayed to a physician, care provider, and the like.

The subject matter disclosed herein may, in some example embodiments, provide a process for quantitation and/or display of pressure and impedance data for segments of the esophagus. This pressure and impedance data may be used to derive segmental luminal changes in cross-sectional area, diameter, and volume for the gastroenterology tract. This data may also allow for the derivation of other physiological parameters, such as work done in transport of food bolus and mechanical properties of the esophagus, such as segmental compliance.

Although the subject matter disclosed herein may be applied to the esophagus, the disclosed subject matter may be applied to measure other areas of the body including segments of gastrointestinal tract from for example the mouth to the anus.

In some example embodiments, pressure and impedance values obtained using an instrument may be converted to parameters that can be used to characterize characteristics of a healthy gastrointestinal tract tissue when moving material along, as well as to monitor the change of a patient's tissue in response to medical treatment in the case of disease or the progression of the disease over time. The instrument may be implemented as a high-resolution manomentry catheter that includes periodically spaced pressure transducers and circuitry to measure impedance. In use, the instrument may sit inside the patient's esophagus, and the instrument may measure characteristics of the patient's body such as pressure applied by the esophagus, and impedance of the patient's chest and esophagus. These esophageal measurements may be performed as a function of time. Some esophageal measurements are performed concurrently with respiratory measurements that indicate the phase of respiration, so that the amount of air in the patient's chest may be factored into the impedance measurements. In some example embodiments, a patient is provided a known quantity of a liquid. This known quantity, or bolus, is swallowed by the patient while the instrument is in the patient's esophagus. During the swallowing event, the bolus travels through the esophagus while the measurements are made. Values that are not measured, but are calculated by an algorithm that accepts measurements as input may include the cross-sectional area along the length of the esophagus as a function of time, work done by segments of the esophagus as a function of time, and the like. These measured and calculated values may then be displayed in, for example, real time to provide a readily discernible graphic to assist physicians, care providers, and the like to differentiate normal physiology from pathology (e.g., disease states) and to pin-point a specific region of the gastrointestinal (GI) tract, specifically the esophagus, which may be of interest or concern.

Though FIG. 1 as well as other examples disclosed herein are described with respect to a patient's esophagus, the system and methods disclosed herein may be applied to other segments of the gastrointestinal tract or other suitable anatomy.

FIG. 1 depicts an example system for quantification of physiological values of a patient, such as a cross-sectional area of an esophagus. The system may include an impedance catheter 110, a data acquisition system 120, a data analysis system 130, a data display system 140, user input 150, and other physiological sensors 160. The impedance catheter 110 may be a high-resolution manometry and impedance catheter.

In some example embodiments, catheter 110 may be fitted inside of the patient (for example in the patient's esophagus). The catheter 110 may measure pressure along the length of the catheter. Multiple measurements may be made, each measurement corresponding to discrete segments of the catheter 110. The pressure may be exerted on the catheter 110 by the surrounding tissue (e.g., the esophagus). When the pressure measurements are being made, the catheter 110 may measure impedance values for discrete segments along the length of the catheter. As will be described in greater detail below, the impedance value may be characteristic of the patient's chest. This may include the tissue surrounding the catheter, any material inside the catheter, and any material inside the esophagus before the beginning of the swallowing event. The catheter 110 sends this pressure and impedance data to the data acquisition system 120, through for example a wired or wireless connection.

The data acquisition system 120 may receive pressure and impedance data from the catheter 110. For example, data acquisition system 120 may receive the data continuously and/or in real-time while the catheter 110 makes the measurements of impedance and pressure, although the data may be received at other times as well. The data acquisition system 120 may store the received data and/or send the received data to the data analysis system 130.

The data acquisition system 120 may include at least one processor circuitry, at least one memory circuitry including code which when executed by the at least one processor provides the operations described herein with respect to the data acquisition system 120.

The data acquisition system 120 may receive an indication of the amount of the liquid (or bolus amount) 150. For example, if a patient swallows 5 milliliters of a liquid, this data may be provided to the data acquisition system 120 to enable some of the calculations described herein. Data from other physiological sensors 160 may also be collected by the data acquisition system 120. For example, a temperature sensor or breathing monitor may send data to the data acquisition system to determine the breathing phase, or patterns, of the patient under test. The patient's breathing patterns may affect the cross-section measurements, so determining the breathing pattern may provide, in some example embodiments, more precise calculation of the values generated by the data analysis system 130.

The data analysis system 130 may include at least one processor circuitry, at least one memory circuitry including code which when executed by the at least one processor provides the operations described herein with respect to the data analysis system.

The data analysis system 130 may receive raw data from the data acquisition system 120, such as a composite impedance value and a pressure value, each for an array of discrete portions of the esophagus. For example, a processing algorithm may determine a cross-sectional area given pressure and impedance measurements and the algorithm may make this determination based on the known bolus value. As described in further detail below, the algorithm may use the length of each segment of the esophagus along which each pressure and impedance measurement is taken. These lengths, in combination with the volume of the bolus taken by the patient during a swallowing event, may allow the algorithm to determine the cross-sectional area of each segment of the esophagus corresponding to an impedance measurement. The resistance of the patient's body may also be taken into account to varying degrees when calculating the cross-sectional area of each segment, and the algorithm may be selected or directed to make assumptions regarding some values, including the resistance of the patient's thoracic area.

This data may be visualized in multiple ways, including pseudo-color maps, in which colors indicate a severity or value for a parameter, such as pressure. In the pseudo-color maps, the x- and y-axes indicate time and location along the catheter 110, respectively. The visualized data may be sent to the data display system 140 for display to a user, such as a clinician, including a doctor, nurse, or technician. The visualized data and plots may be generated by the data analysis system 130 or by the data display system 140.

The data acquisition system 120, data analysis system 130, and the data display system 140 may reside on the same or different processor circuitry, such as a computer and the like. In some example embodiments, some of the data acquisition system 120, data analysis system 130, and the data display system 140 may be on one or more remote servers, such as one or more cloud servers.

The use of manometry and intraluminal ultrasound imaging can show that, a distension wave traversing ahead of a contraction wave, as well as the contraction wave itself, is peristaltic. The cross-sectional area (CSA) of the esophagus is one of several variables that determine intraluminal esophageal impedance value.

Figure 2:
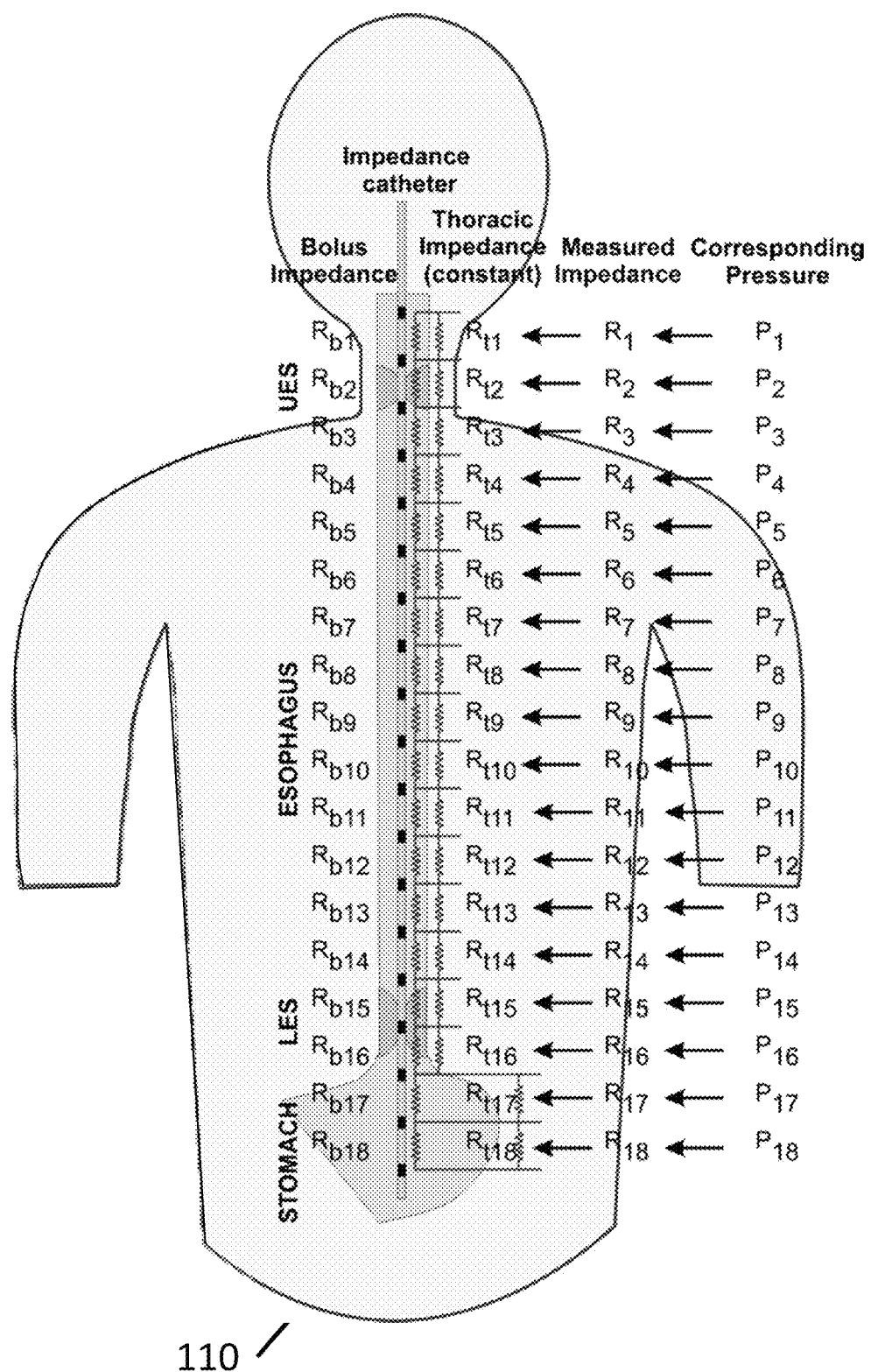
FIG. 2 depicts an example schematic of an impedance catheter inserted in a human along with representative measurements taken along the length of the catheter.

FIG. 2 a schematic of the impendence catheter 110 inside a patient along with values that may be associated with portions of the catheter 110. Along the catheter 110 are segments where the pressure is measured (e.g., $P_1$, $P_2$, $P_3$, . . . ), and between those are segments where impedance is measured. The impedance at each segment is shown include the impedance of the patient's chest (e.g., thoracic impedance, $R_{t1}$, $R_{t2}$, $R_{t3}$, . . . ) surrounding the catheter segment. This value is indicated in FIG. 2 as constant, and in actuality it is nearly constant, but will vary, for example with a patient's breathing. The catheter 110 and data analysis system 130 may also derive the bolus impedance (e.g., $R_{b1}$, $R_{b2}$, $R_{b3}$, . . . ). The calculation of the bolus impedance may factor in changes in impedance due to the patient's breathing pattern or phase. The bolus impedance is the impedance that may be attributed to a volume of liquid that is swallowed. The measured impedance may be a combination of the bolus impedance and the thoracic impedance.

High-resolution manometry may measure the pressure along the catheter using pressure-sensitive solid-state transducers at an interval close enough to be considered high-resolution. The pressure measurements may be overlayed (or compared to) impedance values recorded by the high-resolution manometry. The methods, systems, and apparatus described further herein may utilize known intervals of the sensors along the catheter in combination with approximated values for the resistivity of the patient's tissue and the resistivity of the bolus to approximate a cross-sectional area value for the esophagus at any given time during a swallowing event.

In some example embodiments, intraluminal ultrasound (US) images, impedance, and high-resolution manometry may be used to confirm the relationship between esophageal cross-sectional area (CSA) and intraluminal esophageal impedance values. Intraluminal ultrasound images are ultrasound images taken from inside the esophagus that are used to estimate the dimensions of the esophagus, including the cross-sectional area and the wall thickness, at a known point on the esophagus. Often times, points along the esophagus are described as being above the lower esophageal sphincter (LES) or below the upper esophageal sphincter (UES). For example, the intraluminal ultrasound images can be taken at known points above the LES.

In some example embodiments, impedance derived information in combination with high-resolution manometry data may be used by a data analysis system to calculate relative distension of the esophagus. The display of pressure simultaneously with distension may lead to a display of one parameter over-laid above another as pseudo-color plots, two superimposed plots such that the transparency of one display relative to the other can be altered, or to a 3D-plot depicting the relative change in distension as a diameter and the pressure by pseudo-colors and the like, as described in greater detail elsewhere herein.

In some example embodiments, the methods, systems, and apparatus include generation of plots of pressure-distension loops during a swallowing event for each level of the esophagus. From these plots, the area within the loop represents the relative amount of work done by that segment of the esophagus. In this way, a data analysis system may calculate the total work done, and therefore the percent work done by each segment of the esophagus.

Since it may be determined approximately what volume of liquid was swallowed by a patient, a calculation may be performed to compute the total volume increase in the esophagus before any emptying to estimate the resistivity of the swallowed bolus. Given the resistivity is ρ, then the measured bolus impedance for a given segment i of length L cm is, Ri, and the corresponding lumen cross-section area is Ai and volume Vi. As such, Ri=ρ*L/Ai or Ai=ρ*L/Ri and Vi=Ai*L=ρ*L*L/Ri, and the total increase in volume, V (that corresponds approximately to swallowed volume)= ρ*L*L*sum (1/Ri). In this equation, all other values are known except ρ. A back calculation and check can be performed if the estimated resistivity is close to the measured value.

In subjects with residual esophageal volume (e.g., non-ideal patients), this method would provide the dynamic changes in cross-sectional area. Since the volume in each segment of esophagus may be known (for example, determinable) at some (if not all) time points and the sampling rate is known, a calculation can compute esophageal contents flow velocity change in volume per unit time. This information may inform a caregiver, physician, and the like with the current state of a patient or the relative state of a patient versus a baseline or normal state measured from many normal patients.

For example, analysis of pressure and impedance data may show distension throughout the peristalsis (i.e., an increase in cross-sectional area during the wavelike action of a swallowing event); this analysis may document that there is active inhibition preceding active contraction (i.e., portions of the esophagus do not expand while the portion above it does expand, increasing in cross-sectional area). This analysis may help measure or quantitate this active inhibition, similar to diastolic function of the heart, and thereby differentiate between some of the possible diseases of the esophagus that may be present. This diagnosis, based on the analyzed data, may thereby aid in the development of new therapies and evaluate the effectiveness of each therapy, as well as the progression of the disease over time.

The spacing of electrodes on the catheter may not be equal, or it may be suboptimal to use one constant value for resistivity for all segments of the esophagus. A constant factor for each of the esophagus segments which accounts for segment length and variability in impedance may then be evaluated for each of the segments by examining data at time points after the closure of UES (upper esophageal sphincter) and before the opening of LES (lower esophageal sphincter). The variability in impedance may correlate to measurement accuracy. During this period, some, or most, of the swallowed volume is in the esophagus. Multiple equations, one for each time point, may be written correlating the sum of the volumes calculated for each segment of the esophagus. The volume of each esophageal segment may be calculated using a constant for each esophageal interval multiplied by the inverse of segmental impedance. All of these equations will be equal to the volume of fluid swallowed, as shown below.

These equations can be solved in many ways. A first way involves assuming a constant that accounts for resistivity and other factors for all segments of the esophagus by simply solving a single equation such that all Q values in the equations below are the same. A second way of solving these equations includes finding this constant (e.g., Q) value for each time point as in the first method and then solving the system of equations for any further unknown variables. Another method of solving these equations involves assuming a different Q value by taking multiple equations (same number as the number of esophageal segments between UES and LES) equally spaced in time. At any specific time, the sum of the volumes at each segment of the esophagus measured by the catheter adds up to the total volume swallowed. For example, in the case of 4 time points and 3 or more locations in the esophagus, the following equations describe the impedance of each location (each x value) at a certain time (each y value):

$$Z(1,1)*Q(1)+Z(2,1)*Q(2)+Z(3,1)*Q(3)+ \ldots =\text{Vol}$$

$$Z(1,2)*Q(1)+Z(2,2)*Q(2)+Z(3,2)*Q(3)+ \ldots =\text{Vol}$$

$$Z(1,3)*Q(1)+Z(2,3)*Q(2)+Z(3,3)*Q(3)+ \ldots =\text{Vol}$$

$$Z(1,4)*Q(1)+Z(2,4)*Q(2)+Z(3,4)*Q(3)+ \ldots =\text{Vol}$$

where $Z(s,t)$ is the calculated impedance of the liquid at location, s, in the esophagus at time, t, and $Q(s)$ is the constant Q at location, s.

The assumption is that the volume of the swallowed liquid never changes as it proceeds through the esophagus at different locations, so the volume (Vol) is about the same numerical constant on the right hand side of each equation above. In some experiments, Vol has a value of 5 ml for usual size swallows, although other bolus sizes may be used as well.

The impedance values, Z, are calculated using parallel resistance equations, so the impedance values may be treated as known numerical values. Alternatively or additionally, the values of Q may be derived as a solution to these equations describing the impedance as a function of time and location. The impedance values, Z, may be then calculated using linear programming (or other processing/numerical techniques). The limits that are established when determining Q for each time point may serve as limits or constants in the system of equations that solve for the impedance values.

The impedance calculations may be done using a data analysis system, such as data analysis system 130 described above. The calculations may be done in a programmatically driven system, such that minimal user input is required, including the case where the data analysis system programmatically completes the calculations. This generation of calculations in turn allows for programmatic generation of visual representations of the data and analyzed data, including cross-sectional area, work done, and the like. Because of the complexity of the calculation to the equations above and the real-time nature of the measurements, it would be unlikely (if not impossible) for the calculations to be performed manually, so a computer-based technique may be required.

Pressure and impedance data obtained and analyzed as described above may provide a way to better understand the role each portion of the esophagus plays in propulsion of the food down the esophagus. This data may also yield a better understanding of the normal physiology of propulsion. That is to say such data and analysis may help physicians to understand what normal swallowing looks like and to understand the characteristics of various diseases of the esophagus in relation to normal swallowing. Once these tools are available the efficacy of various drug treatments may be evaluated and better drugs to treat various diseases may be developed.

In an example experiment, using 15 normal healthy subjects, impedance and manometry were measured along the whole length of the esophagus using a high-resolution manometry catheter. Swallowing events that included swallow induced primary peristalsis was recorded using 5 ml bolus of 0.5 N saline. Peristalsis is the wavelike motion used by the human body to move fluid or material through the esophagus. Ultrasound (US) images were recorded at 4 cm and 14 cm above the LES. Impedance data were exported to a spreadsheet software program and analyzed for the baseline and lowest bolus impedance value at each level of the esophagus. Cross-sectional area of the esophagus at 4 and 14 cm above the LES of the esophagus were measured from the US images.

Figure 3A:
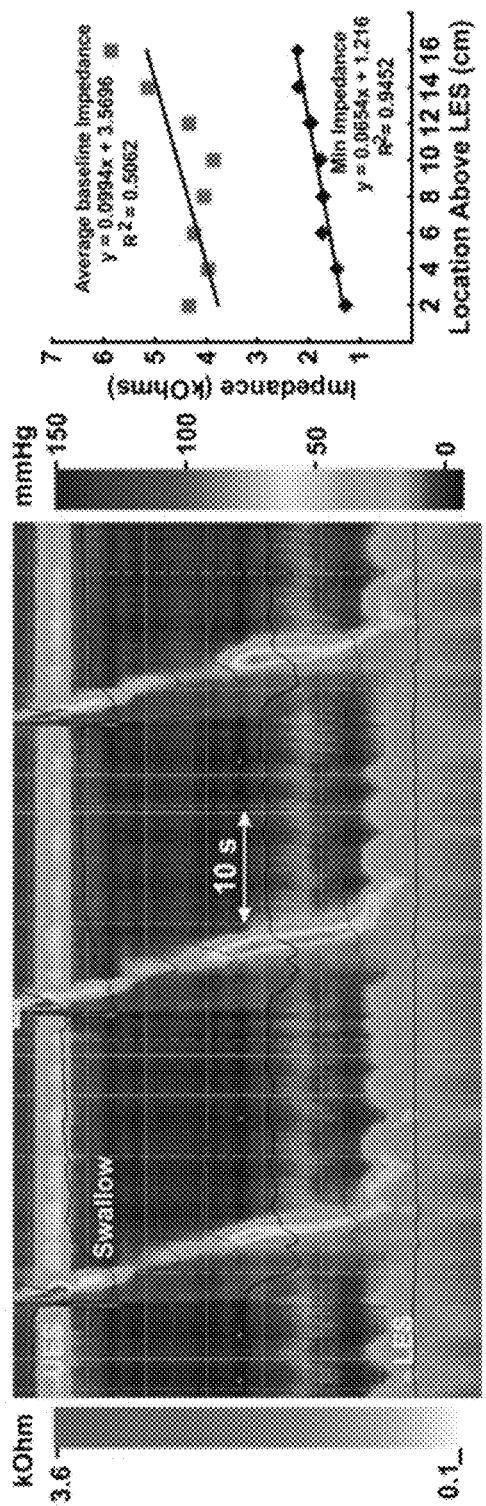
FIG. 3A depicts impedance versus time and location data, pressure versus time and location data, and average impedance ranges as a function of location for a patient.

In this example, impedance recordings show that following a swallow, the onset of a drop in impedance, as well as nadir impedance, traversed the esophagus in a sequential fashion in front of the contraction wave as depicted at FIG. 3A. In the left-hand portion of FIG. 3A, a pseudo-color map of the pressure and impedance overlays the pressure in the esophagus of a patient over time for multiple swallowing events. The top of the pseudo-color map corresponds to the UES and the bottom corresponds to the LES and stomach. The color scale for pressure is on the right hand side of the pseudo-color map, and the scale for impedance is on the left hand side. The right-hand portion of the pseudo-color map shows a linear representation of impedance maximum values and minimum values as a function of location along the esophagus.

The data from the example experiment represented a strong linear relationship between the location and nadir impedance value such that the lowest impedance values are located just above the LES, with a difference of approximately 100 ohms every 1 cm along the length of the esophagus (right-hand portion of FIG. 3A). Atropine injected intravenously (e.g., 10 µgm/kg) abolished esophageal contractions, reduced baseline esophageal impedance, and abolished sequential progression of nadir impedance along the esophagus. Ultrasound image analysis showed that peak distension corresponded with nadir impedance value. Similar to bolus nadir impedance, peak distension recorded by ultrasound imaging traversed the esophagus in a peristaltic fashion. Ultrasound images show greater esophageal distension at 4 cm compared to 14 cm above the LES, with cross-sectional area values of 1400 versus 600 mm$^2$ respectively. This example experiment may show that (1) intraluminal distension and contraction wave during peristalsis are tightly linked and (2) intraluminal impedance recording is a relatively simple technique to record luminal distension of the esophagus.

Although some of the examples disclosed herein refer to the esophagus, the subject matter disclosed herein may be applied to other segments of the gastrointestinal (GI) tract, for example as the colon and the like.

Figure 3B:
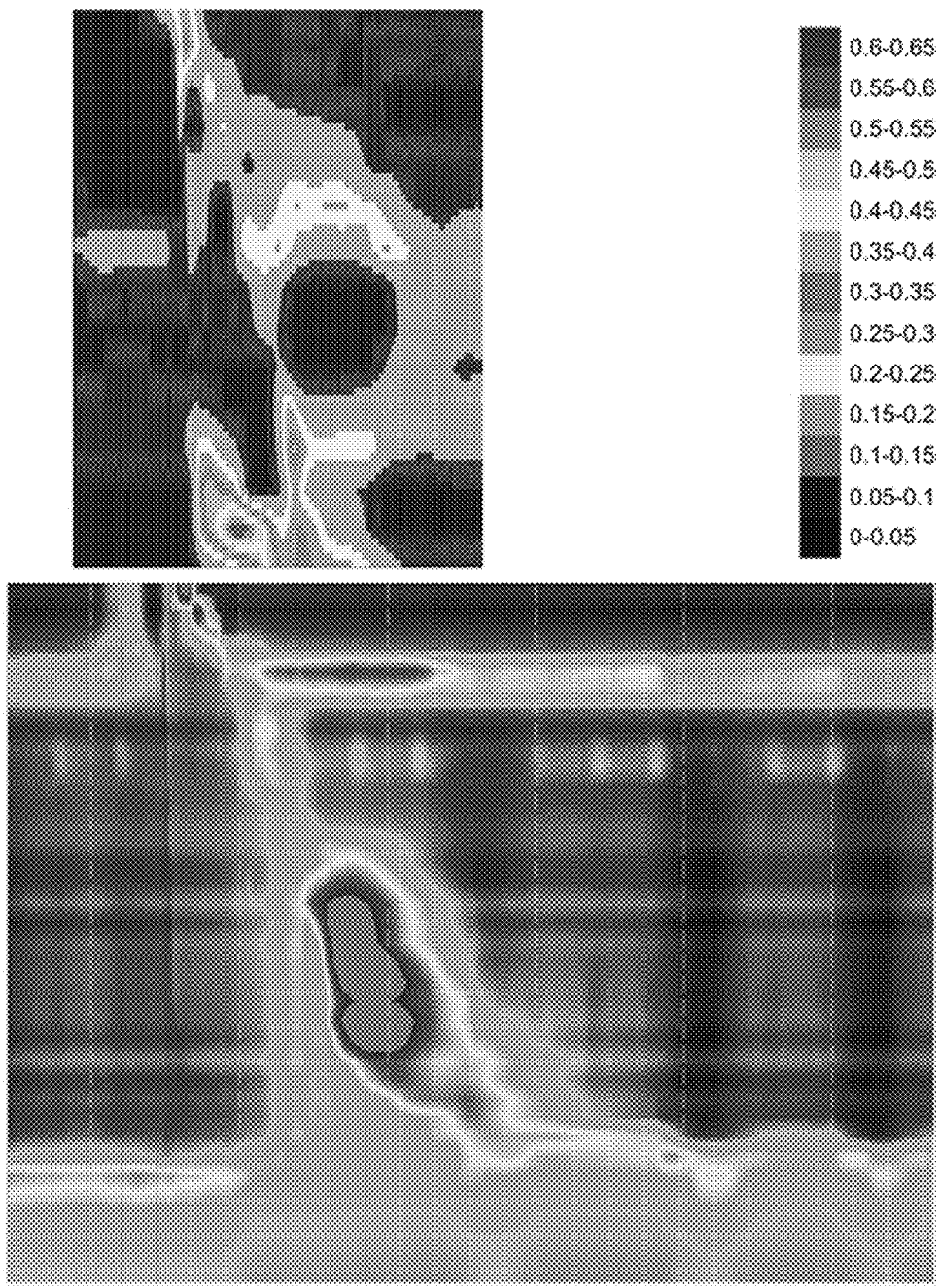
FIG. 3B depicts a pseudo-color diameter/luminal cross-sectional quantitated area plot along with a high resolution manometry plot.

FIG. 3B shows another plot depicting the quantitated pseudo-color diameter/luminal cross-sectional area plot (top panel) along with the high-resolution manometry plot (lower panel). The two plots are temporally aligned. They may be displayed one above the other (as shown) or may be superimposed with either plot being variably translucent. Along with the variation in transparency, the superimposed plots may show multiple swallowing events. The plots may change the time frame shown by scrolling or some other advancement technique.

Figure 3C:
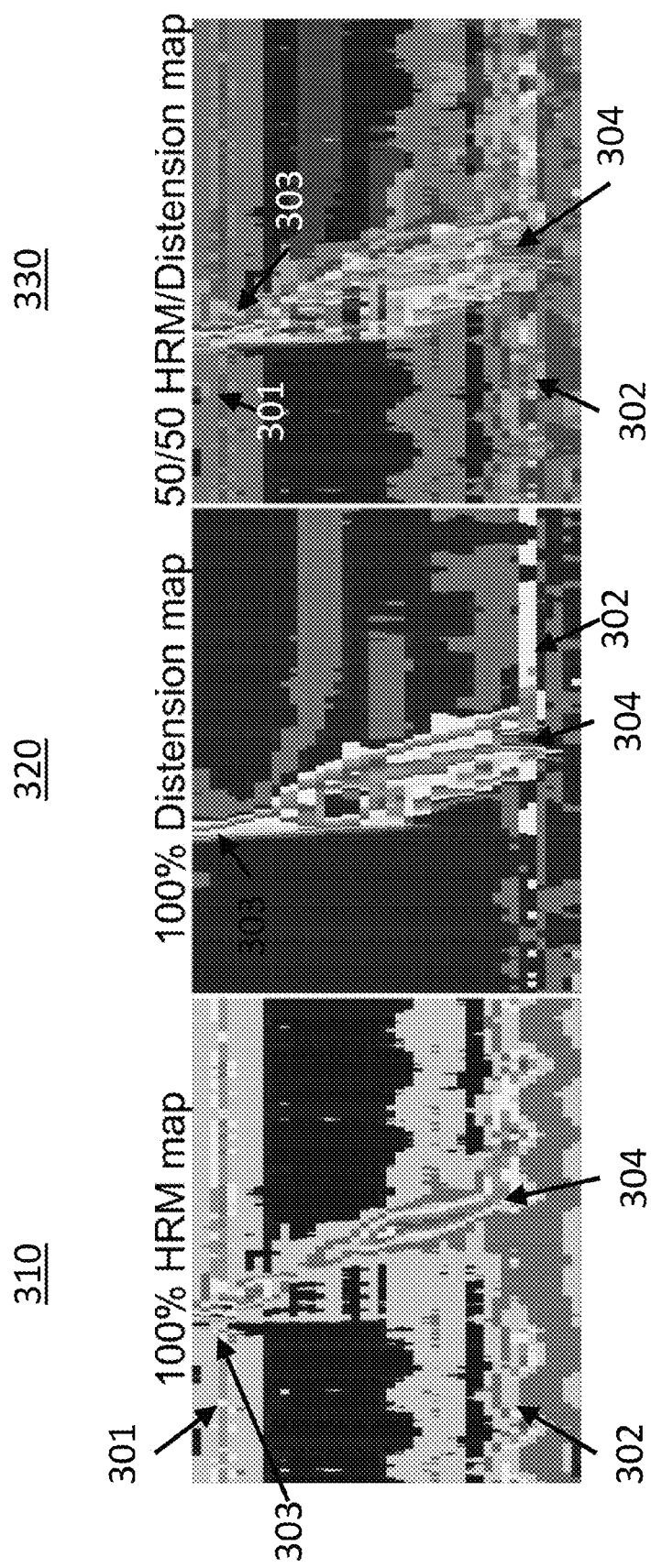
FIG. 3C depicts an example of one type of simultaneous visualization of pressure and calculated cross-sectional area data.

FIG. 3C depicts three views of data. The left-most view 310 shows high-resolution manometry (HRM) data for a swallowing event as a pseudo-color map. On the map, the upper esophageal sphincter (UES) 301, the lower esophageal sphincter (LES) 302, the start of the swallow 303, and the end of the swallowing event 304 are shown. The middle view 320 shows the lower esophageal sphincter (LES) 302, the start of the swallow 303, and the end of the swallowing event 304 on a pseudo-color map that represents the degree of increase in the cross-sectional area (i.e., distension) of the esophagus. The right-most view 330 shows an overlay of the distension data 320 over the HRM data 310, with the distension data 320 being 50% transparent. In the 50/50 view 330, the upper esophageal sphincter (UES) 301, the lower esophageal sphincter (LES) 302, the start of the swallow 303, and the end of the swallowing event 304 are shown.

Figure 4A:
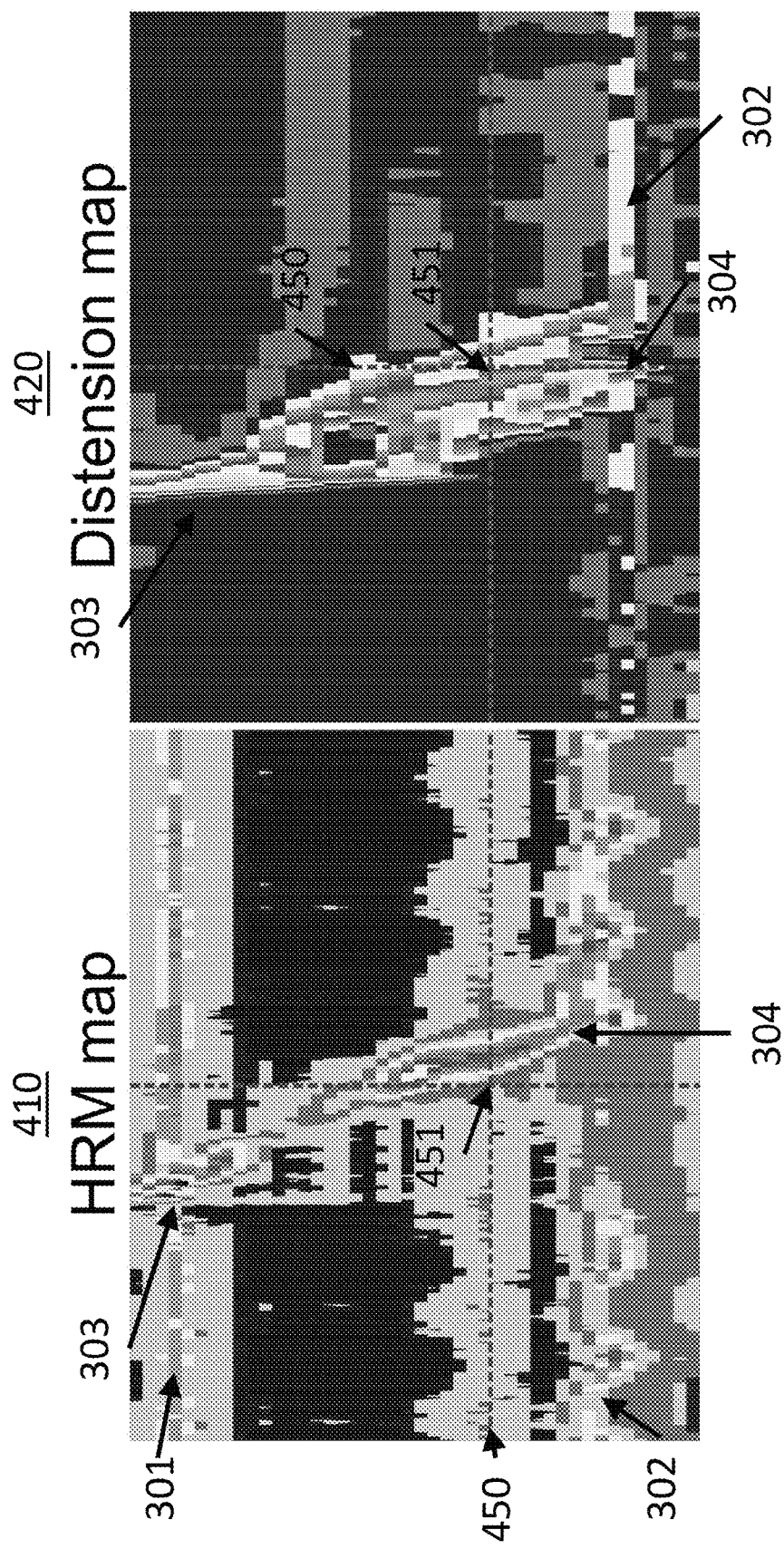
FIGS. 4A and 4B depict another example of simultaneous visualization of pressure and calculated cross-sectional area data.

FIG. 4A depicts a side-by-side view of a high-resolution manometry pseudo-color map 410 and a distension pseudo-color map 420. Both types of pseudo-color maps show the lower esophageal sphincter (LES) 302, the start of the swallow 303, and the end of the swallowing event 304, as well as axis indicators 450 and a data point indicator 451. The data point indicator 451 may identify the same point in time and along the esophagus in each map. In some embodiments, the numerical data corresponding to the identified point on each map may be shown by the data display system. Alternatively or additionally, when a user selects a data point that is identified by the data point indicator 451, the pressure versus cross-sectional area/volume loop plots may appear in a new view. When the maps are viewed side-by-side, it may be easier to compare identical positions along the esophagus in each map.

Figure 4B:
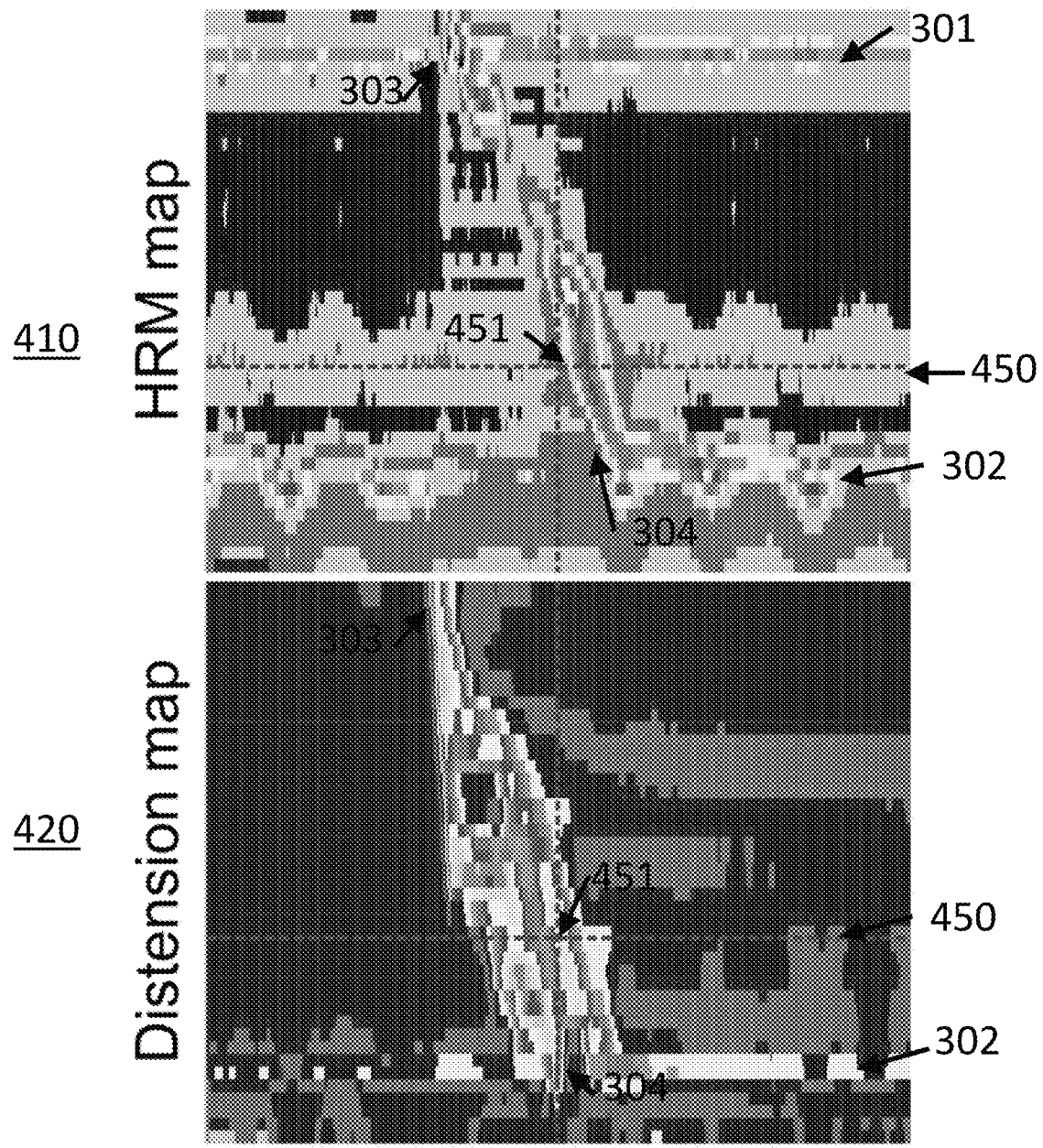
Figure 4C:
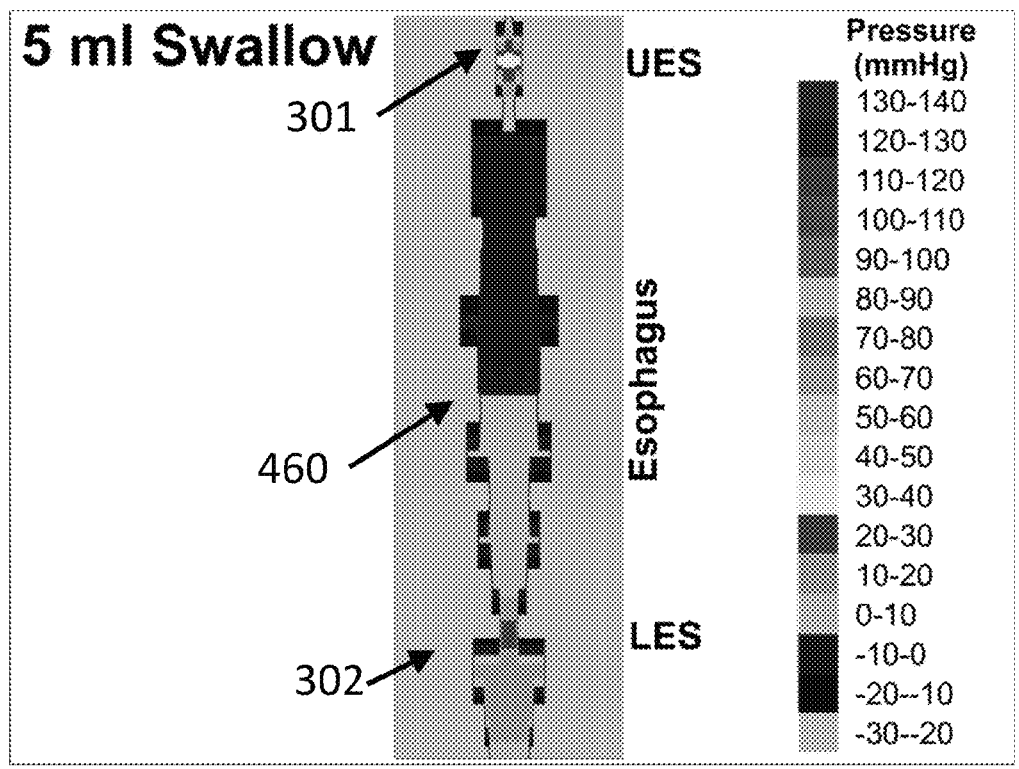
FIGS. 4C-4H depict a visualization of location along a patient's esophagus, cross-sectional area, and pressure at given time points that may be combined to create an animated view.
Figure 4D:
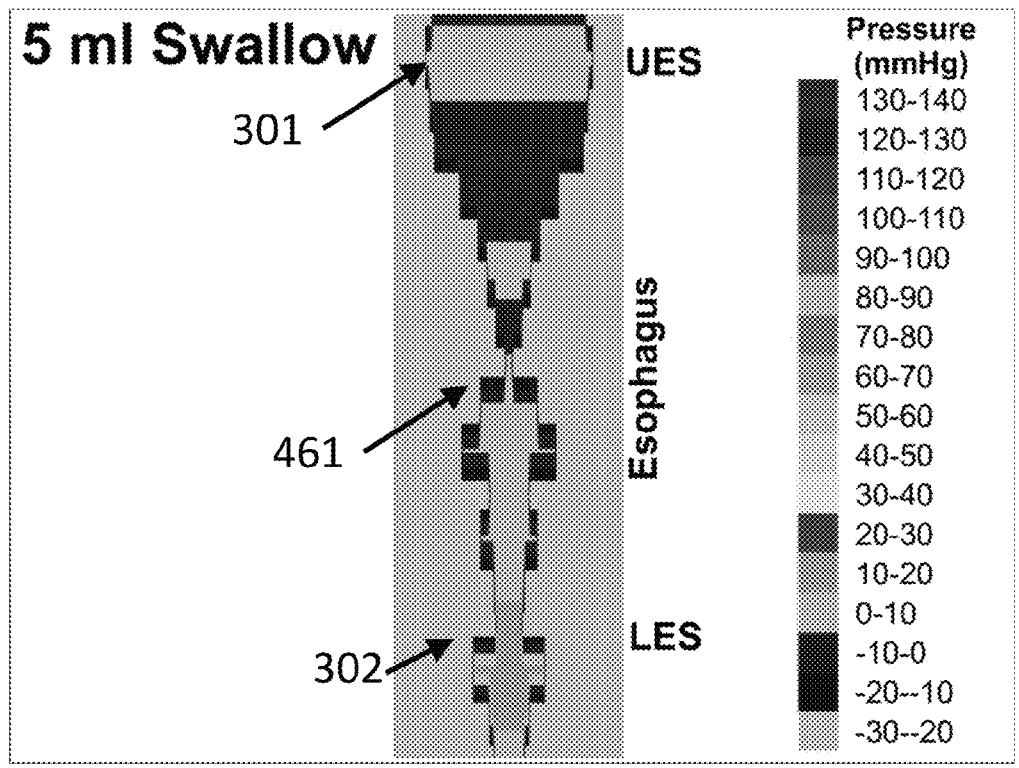
Figure 4E:
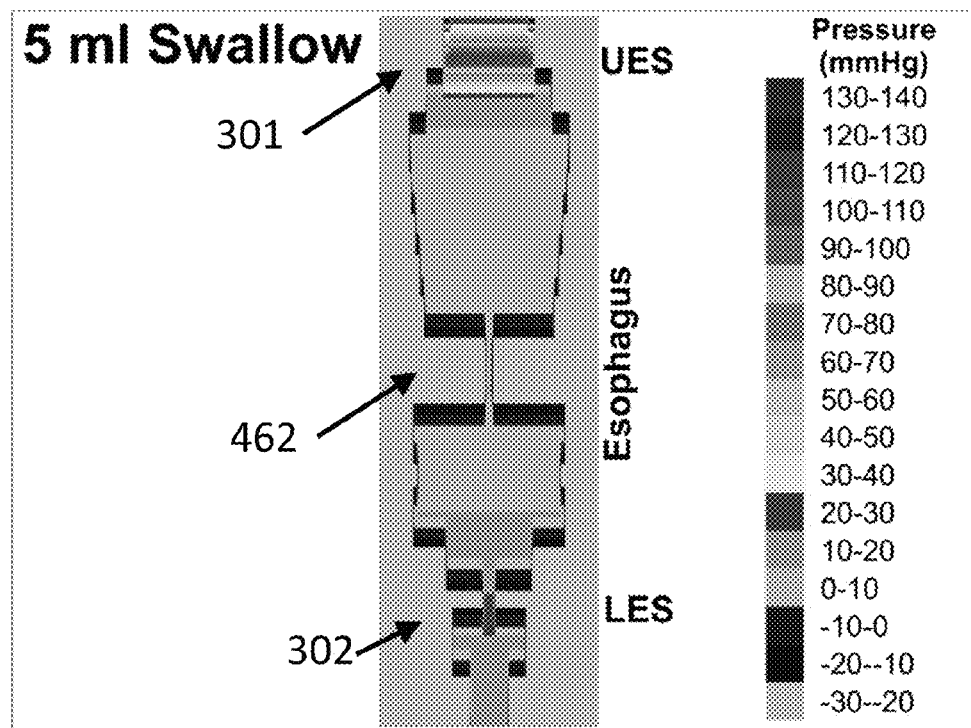
Figure 4F:
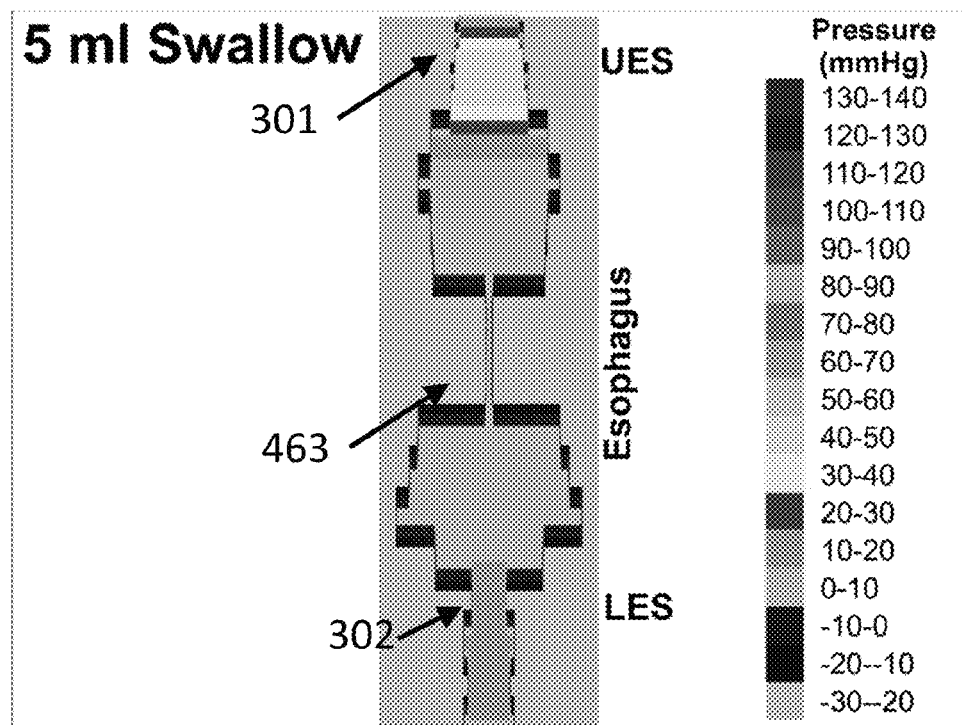
Figure 4G:
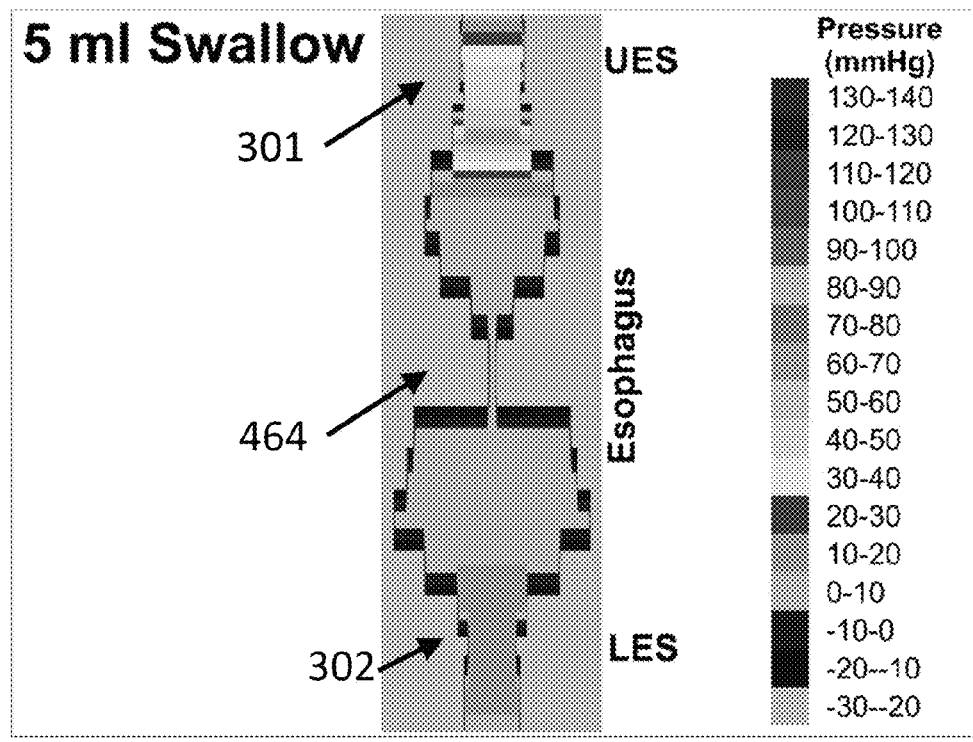
Figure 4H:
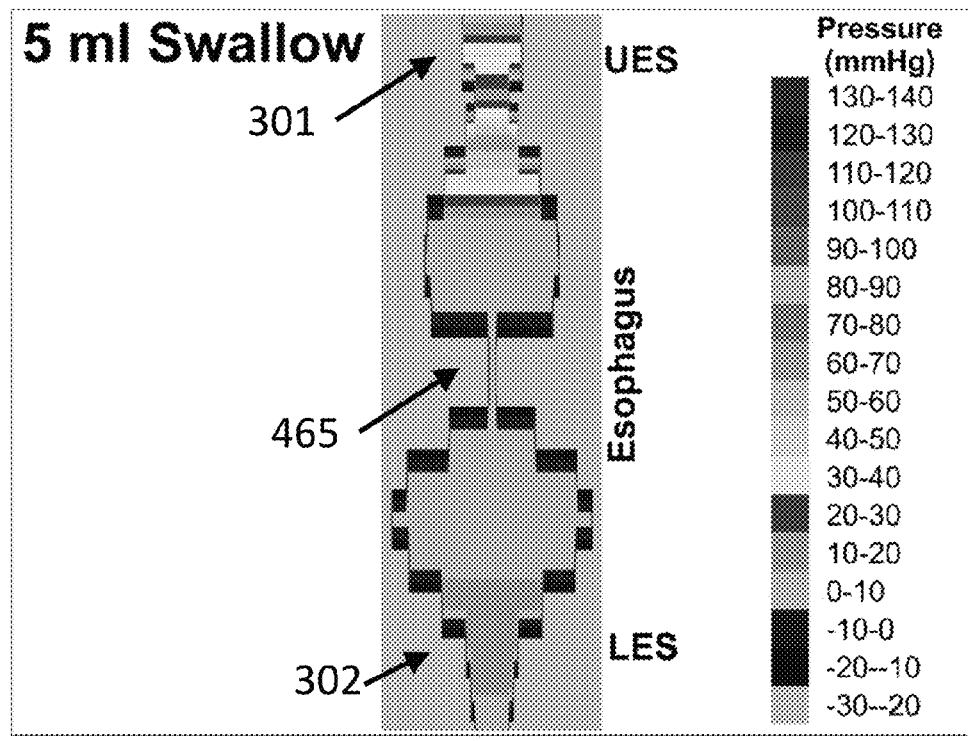

FIG. 4B depicts a stacked view of a high-resolution manometry pseudo-color map 410 and a distension pseudo-color map 420. As in FIG. 4A, both types of pseudo-color maps show the lower esophageal sphincter (LES) 302, the start of the swallow 303, and the end of the swallowing event 304, as well as axis indicators 450 and a data point indicator 451. The data point indicator 451 may identify the same point in time and along the esophagus in each map. In some embodiments, the numerical data corresponding to the identified point on each map may be shown by the data display system. As in FIG. 4A, when a user selects a data point that is identified by the data point indicator 451, the pressure versus cross-sectional area/volume loop plots may appear in a new view. When the maps are viewed one over the other, with the axis indicating time aligned, it may be easier to compare the distension and pressure at identical time points.

The pseudo-color impedance and pressure plots may have the ability to keep all values transparent except one or a range of pressure or impedance values. This may result in iso-pressure or iso-impedance (uncorrected or corrected for thoracic impedance) plots superimposed on each other. This may allow for the examination of the relationship of high pressure exerted by the esophagus versus maximum impedance along the esophagus, minimum cross-sectional area, maximal distension (minimum impedance) and corresponding pressures, or any combination thereof.

FIGS. 4C-4H depict a visualization of location along a patient's esophagus, cross-sectional area as a cross-sectional diameter, and pressure at given time points during a swallowing event that may be combined to create an animated view. Each visualization represents a cross-sectional view of the patient's esophagus at a given time point. There is a fixed time difference between visualizations, for example 0.3 seconds between FIGS. 4C and 4D. Along the esophagus, the upper esophageal sphincter (UES) 301 and the lower esophageal sphincter (LES) 302 are labeled and act as points of reference that are in the same location in each visualization. Depending on the number of pressure sensors and impedance circuits along the length of the esophagus, the representation of the esophagus may have more or less rough edges.

For example, FIGS. 4C-4H, show six time points for a patient's esophagus. Viewing these figures in quick succession shows how a point 460 expands then contracts 461, and then may have about the same cross-sectional area (shown as a diameter in these two-dimensional figures) 462, 463, 464, 465. The progression of cross-sectional area 460, 461, 462, 463, 464, 465 may be accompanied by a progression in pressure. A clinician or physician may use this information to observe distension of the esophagus as a whole, in certain points, and with respect to the amount of pressure exerted. Though discussed as a two-dimensional rendering and animated representation, three-dimensional representation of a patient's esophagus may be created and displayed.

Additionally or alternatively, though various visualizations and representations are discussed with respect to a single patient's esophagus and single swallowing event, the visualizations and representations may represent average data. The data, or values calculated from measured data, may be averages of many normal patients, such as to establish base-line behavior. The average of multiple swallowing events for the same patient may also be displayed. The average of multiple swallowing events for many patients of a similar type (e.g., normal patients, patients of the same age range, patients diagnosed with the same disease) may also be displayed.

Figure 5:
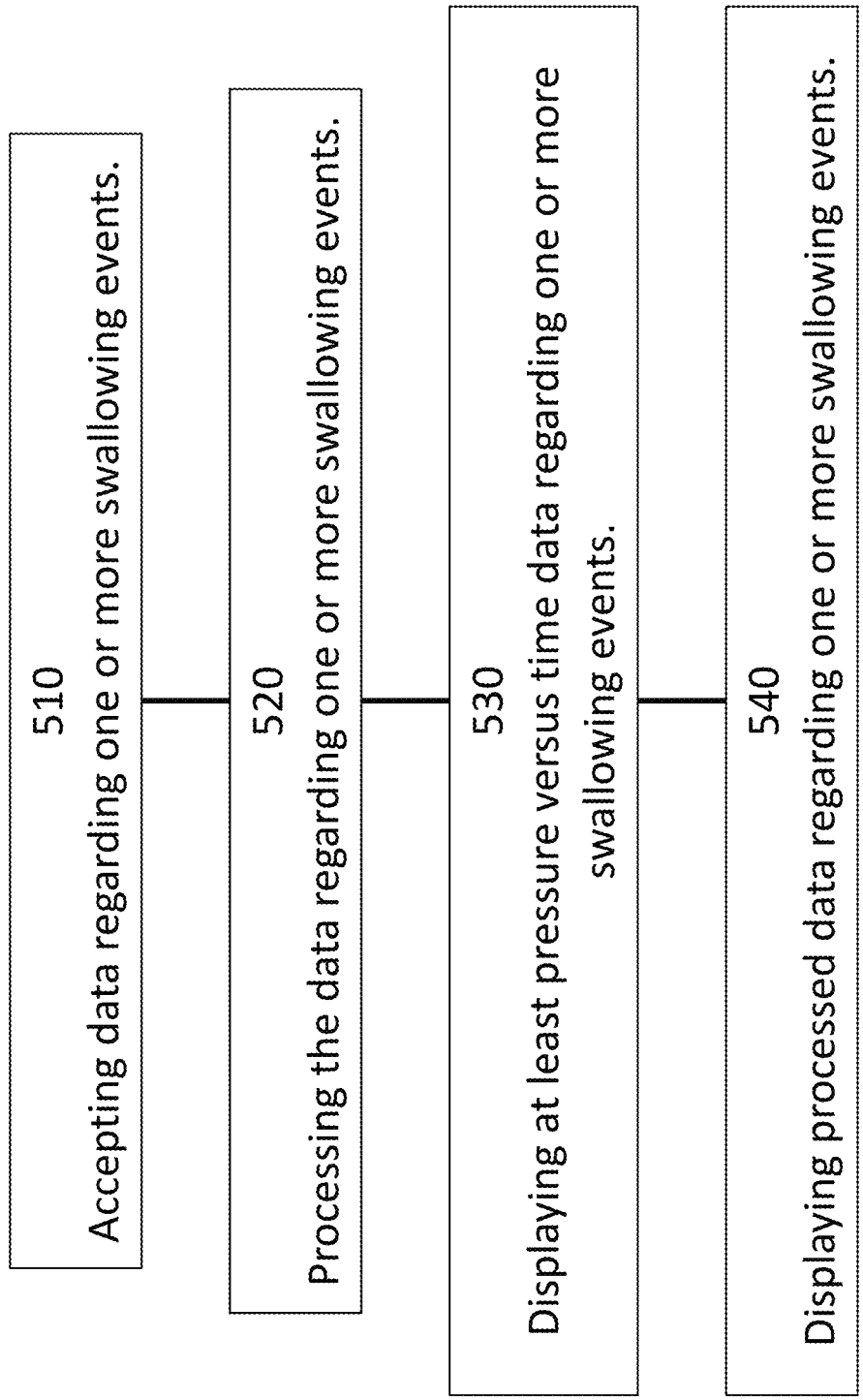
FIG. 5 depicts a method for processing and displaying data from an esophageal catheter.

A method utilizing the systems and apparatus described above is shown in FIG. 5. In the method, the data acquisition system accepts or receives data regarding one or more swallowing events, as in 510. The data may come from a catheter, such as a high-resolution manometry catheter. The data acquisition system may in turn pass the data to a data analysis system for processing, as in 520. Analysis and processing of the data from the one or more swallowing events may include the determination of cross-sectional area, work done, resistivity, and the like, described above. The data acquisition system may receive data in a real-time, or near-real-time, fashion. In turn, the data acquisition system may store the data, or it may pass it along to the data analysis system with the same timing as it is received.

The data analysis system passes the analyzed data along to the data display system and displays at least the pressure versus time data for the one or more swallowing events, as in 530. The data analysis system may utilize one or more algorithms to calculate the cross-sectional area for each segment, as well as work done by the esophagus at each segment. The one or more algorithms may use the volume of a bolus taken by the patient at the start of each swallowing event, a known or estimated resistivity for the patient's tissue, a known length for each segment the esophagus, and an impedance measurement for each segment of the esophagus to make those calculations, as described above. Additionally or alternatively, the data display system may display processed data, that is the cross-sectional area, a diameter derived from the cross-sectional area, pressure area/volume loops for each segment of the esophagus, work done, resistivity, and the like, as in 540. The pressure versus time data (e.g., HRM data versus time) may have the processed data displayed alongside, in a stack configuration, or overlaid on it, as described above. Data processing may occur concurrently with data acquisition. Data processing may occur as a post-process, off-line, after the data has been received by the data acquisition system, although the data processing may occur at other times as well.

The systems and methods disclosed herein may be embodied in various forms including, for example, a data processor, such as for example a computer that also includes a storage, digital electronic circuitry, firmware, software, or in combinations of them. Moreover, the above-noted features and other aspects and principles of the present disclosed embodiments may be implemented in various environments. Such environments and related applications may be specially constructed for performing the various processes and operations according to the disclosed embodiments or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the disclosed embodiments, or it may be more convenient to construct a specialized apparatus or system to perform the required methods and techniques.

The systems and methods disclosed herein may be implemented as a computer program product, i.e., a computer program tangibly embodied in an information carrier, e.g., in a machine readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

The foregoing description is intended to illustrate but not to limit the scope of the invention, which is defined by the scope of the appended claims. Other embodiments are within the scope of the following claims.

What is claimed:

1. A method comprising:

measuring, by an impedance and high resolution manometry catheter in an esophagus, data representative of a pressure and/or an impedance associated with a plurality of swallowing events, the impedance and high resolution manometry catheter having a plurality of segments, and the data being measured by one or more electrodes disposed at each of the plurality of segments;

determining, based on the data measured by the impedance and high resolution manometry catheter and a predetermined amount of a bolus consumed during each of the plurality of swallowing events, a cross-sectional area of the esophagus;

determining, based on the cross-sectional area and a segment pressure from the plurality of swallowing events, an average value for work done by a segment of the esophagus, the segment pressure being exerted by the segment of the esophagus, and the bolus consumed having a same volume for each of the plurality of swallowing events;

generating a display of the determined cross-sectional area; and presenting the generated display, wherein the generated display includes at least a plot of the segment pressure exerted by the segment of the esophagus as a function of location along the segment of the esophagus and as a function of time.

2. The method of claim 1, further comprising:

receiving an indication of the predetermined amount of the bolus, wherein the data is representative of the pressure and the impedance associated with the plurality of swallowing events; and determining an esophageal impedance.

3. The method of claim 2, wherein the determining of the average value further comprises:

generating the plot of the segment pressure versus a cross-sectional area loop for the segment of the esophagus at discrete time points for each of the plurality of swallowing events; and determining another area for the segment pressure for each of the plurality of swallowing events versus cross-sectional area loop plotted.

4. The method of claim 1, further comprising:

determining a reference average work for two or more patients identified as normal to generate a reference work profile.

5. The method of claim 4, further comprising:

comparing the work done by the segment of the esophagus of a patient with a disease with the reference work profile.

6. The method of claim 1, further comprising:

determining another average value for segmental compliance of the segment of the esophagus, the determining of the another average value based on the cross-sectional area or esophageal segmental volume, and further based on the segment pressure exerted by the segment of the esophagus.

7. The method of claim 1, further comprising:

rendering, as a time-lapse movie, at least one of the cross-sectional area, a cross-sectional diameter, or the segment pressure.

8. The method of claim 1, wherein a plurality of cross-sectional area calculations for a plurality of segments of the esophagus are each based on the predetermined amount of the bolus.

9. The method of claim 1, wherein the data representative of the pressure and/or the impedance associated with the plurality of swallowing events comprises information from a plurality of pressure transducers disposed along a length of the impedance and high resolution manometry catheter.

10. The method of claim 9, wherein the segment pressure is measured by a subset of the plurality of pressure transducers.

11. A system comprising:
an impedance and high resolution manometry catheter configured to at least measure, in an esophagus, data representative of a pressure and/or an impedance associated with a plurality of swallowing events, the impedance and high resolution manometry catheter having a plurality of segments, and the data being measured by one or more electrodes disposed at each of the plurality of segments;
at least one processor; and
at least one memory including program code which when executed by the at least one processor provides operations comprising:
determining, based on the data measured by the impedance and high resolution manometry catheter and a predetermined amount of a bolus consumed during each of the plurality of swallowing events, a cross-sectional area of the esophagus;
determining, based on the cross-sectional area and a segment pressure from the plurality of swallowing events, an average value for work done by a segment of the esophagus, the segment pressure being exerted by the segment of the esophagus, and the bolus consumed having a same volume for each of the plurality of swallowing events;
generating a display of the determined cross-sectional area; and
presenting the generated display, wherein the generated display includes at least a plot of the segment pressure exerted by the segment of the esophagus as a function of location along the segment of the esophagus and as a function of time.

12. The system of claim 11, further comprising:
receiving an indication of the predetermined amount of the bolus, wherein the data is representative of the pressure and the impedance associated with the plurality of swallowing events; and
determining an esophageal impedance.

13. The system of claim 12, wherein the determining of the average value further comprises:
generating the plot of the segment pressure versus a cross-sectional area loop for the segment of the esophagus at discrete time points for each of the plurality of swallowing events; and
determining another area for the segment pressure for each of the plurality of swallowing events versus cross-sectional area loop plotted.

14. The system of claim 11, further comprising:
determining a reference average work for two or more patients identified as normal to generate a reference work profile.

15. The system of claim 14, further comprising:
comparing work done by the segment of the esophagus of a patient with a disease with the reference work profile.

16. The system of claim 15, further comprising:
determining another average value for segmental compliance of the segment of the esophagus, the determining of the another average value based on the cross-sectional area or esophageal segmental volume, and further based on the segment pressure exerted by the segment of the esophagus.

17. The system of claim 11, further comprising:
rendering, as a time-lapse movie, at least one of the cross-sectional area, a cross-sectional diameter, or the segment pressure.

18. The system of claim 11, wherein the data representative of the pressure and/or the impedance associated with the plurality of swallowing events comprises information from a plurality of pressure transducers disposed along a length of the impedance and high resolution manometry catheter.

19. The system of claim 18, wherein the segment pressure is measured by a subset of the plurality of pressure transducers.

20. The system of claim 11, wherein a plurality of cross-sectional area calculations for a plurality of segments of the esophagus are each based on the predetermined amount of the bolus.

* * * * *